US 6,536,946 B1

(12) United States Patent
Froelich et al.

(10) Patent No.: US 6,536,946 B1
(45) Date of Patent: Mar. 25, 2003

(54) DEVICE AND METHOD FOR DIRECTLY MEASURING CALORIFIC ENERGY CONTAINED IN A FUEL GAS

(75) Inventors: Benoit Froelich, Marly le Roi (FR); Didier Dominguez, Oslo (NO)

(73) Assignee: Schlumberger Industries, S.A. (FR)

( * ) Notice: Subject to any disclaimer, the term of this patent is extended or adjusted under 35 U.S.C. 154(b) by 0 days.

(21) Appl. No.: 09/623,812
(22) PCT Filed: Mar. 13, 1999
(86) PCT No.: PCT/FR99/00659
§ 371 (c)(1),
(2), (4) Date: Sep. 8, 2000
(87) PCT Pub. No.: WO99/49299
PCT Pub. Date: Sep. 30, 1999

(30) Foreign Application Priority Data

Mar. 24, 1998 (FR) .............................. 98 03718

(51) Int. Cl.[7] .................................. G01N 25/22
(52) U.S. Cl. .................................. 374/36; 73/23.2
(58) Field of Search .................. 374/36; 356/437; 250/343; 73/23.2, 30.1, 24.05; 702/30

(56) References Cited

U.S. PATENT DOCUMENTS

| 4,384,792 A | * | 5/1983 | Sommers et al. ............. 374/36 |
| 4,845,976 A | * | 7/1989 | Johnson et al. ............... 73/23 |
| 5,005,402 A | * | 4/1991 | Pischinger et al. .......... 324/663 |
| 5,100,244 A | * | 3/1992 | Kniebes ...................... 374/36 |
| 5,488,227 A | * | 1/1996 | Sweet ......................... 250/343 |
| 5,807,749 A | * | 9/1998 | Hornemann ................. 436/143 |
| 5,822,058 A | * | 10/1998 | Adler-Golden et al. ..... 356/300 |
| 6,157,455 A | * | 12/2000 | Pindivic et al. ............. 356/437 |
| 6,244,097 B1 | * | 1/2001 | Schley et al. ................ 73/23.2 |
| 6,279,380 B1 | * | 8/2001 | Van Wesenbeeck et al. ........................ 73/25.01 |
| 6,420,695 B1 | * | 7/2002 | Grasdepot et al. .......... 250/226 |
| 6,442,996 B1 | * | 9/2002 | Thurston et al. ........... 73/24.01 |
| 6,446,487 B1 | * | 9/2002 | Van Wesenbeeck et al. . 73/23.2 |

FOREIGN PATENT DOCUMENTS

| DE | 19921167 A1 | * | 8/2000 | |
| WO | WO 99/10740 | * | 3/1999 | .......... G01N/33/22 |

* cited by examiner

Primary Examiner—Diego Gutierrez
Assistant Examiner—Lydia M. De Jesús
(74) Attorney, Agent, or Firm—Straub & Pokotylo; Michael P. Straub

(57) ABSTRACT

The invention concerns a device (10) for measuring calorific energy contained in a fuel gas transported in a pipe (16) comprising a gas meter (12) measuring a volume V in pressure conditions P and temperature conditions T of a gas circulating in said pipe and an apparatus (14;52;63) to determine the gas calorific power H. The invention is characterized in that said apparatus for determining calorific power measures at least one physical variable proportional to the number of molecules of the gas different constituents in a given volume and is placed as near as possible to the gas meter so as to determine the calorific power H(P,T) in similar pressure P and temperature T conditions as those wherein the gas volume V(P,T) is measured, said device then determining the calorific energy H(P,T) V(P,T) contained in the gas.

26 Claims, 2 Drawing Sheets

DEVICE AND METHOD FOR DIRECTLY MEASURING CALORIFIC ENERGY CONTAINED IN A FUEL GAS

FIELD OF THE INVENTION

The invention concerns a device for direct measurement of the calorific energy contained in a combustible gas transported in a pipe comprising a gas meter to measure the volume V of gas under the pressure P and temperature T conditions of the gas circulating in said pipe and an apparatus for determination of the calorific value H of the gas.

BACKGROUND OF THE INVENTION

Processes exist for the measurement of the energy contained in a combustible gas, such as natural gas for example, transported in a pipe.

To this end, an apparatus such as a chromatograph or a calorimeter is generally placed at a given point in the pipe and used to determine the calorific value H of the gas from a gas sample taken in said pipe and adjusted to normal pressure $P_0$ and temperature $T_0$ conditions.

The calorific value H is therefore determined under these conditions.

A gas meter placed at another point in the pipe, generally downstream to the apparatus, measures a volume V of gas under the pressure P and temperature T conditions of the gas circulating in said pipe at the point where measurement of volume takes place.

Moreover, an apparatus for correction of pressure and temperature and, in some cases, of the compressibility coefficient, is attached to the gas meter and transforms the gas volume V measured under pressure P and temperature T conditions to a volume $V_0$ adjusted to normal pressure $P_0$ and temperature $T_0$ conditions.

A pressure sensor and a temperature sensor are required to carry out this correction for the volume V.

The calorific energy contained in a gas is therefore equivalent to the multiplication $H.V_0$.

However, this technique for measuring the calorific energy of a gas has a number of disadvantages as it requires the use of a pressure and temperature correction apparatus, as well as pressure and temperature sensors, in addition to the apparatus for measurement of calorific value (chromatograph, calorimeter . . . ) which can be costly.

Consequently, it would be useful to be able to measure the calorific energy of a combustible gas using a method that is simpler than previous methods.

SUMMARY OF THE INVENTION

The object of this invention is therefore a device for direct measurement of the calorific energy contained in a combustible gas transported in a pipe comprising a gas meter measuring the volume V of gas under pressure P and temperature T conditions of the gas circulating in said pipe and an apparatus for determination of the calorific value H of the gas, characterised in that said apparatus for determination of the calorific value measures at least one physical quantity proportional to the number of molecules of the various constituents of the gas in a given volume and is placed as close to the gas meter as possible in order to determine the calorific value H(P,T) under the same pressure P and temperature T conditions as those in which the volume V(P,T) of the gas is measured, said device then being used to determine the calorific energy H(P,T) V(P,T) contained in the gas.

The device according to the invention does not require the use of a pressure and temperature correction apparatus and therefore measurement of pressure and temperature is no longer necessary in order to determine the calorific value of a gas.

This is possible, on the one hand, since determination of calorific value is carried out at a point where the volume of gas measured under the same temperature and pressure conditions and, oil the other hand, by measuring a physical quantity proportional to the various constituents of the gas in a given volume.

Measurement of a physical quantity directly gives the number of molecules present in a given volume at a given pressure and temperature.

If pressure or temperature vary, the number of molecules in a given volume varies according to the formula $n=PV/ZRT$ where Z is the compressibility coefficient of the gas and R is the Boltzmann constant, and the physical quantity also varies in the same proportion.

Consequently, this physical quantity measures the number of molecules of the various constituents of a gas independently of pressure and temperature.

Advantageously, the physical quantity measured is the absorbance of electromagnetic radiation by at least one combustible constituent present in a large proportion in the gas and for at least one wavelength of said radiation.

The apparatus then deduces the calorific value of this absorbance measurement.

Moreover, the choice of this particular physical quantity is very useful since it does not require contact with the gas.

The choice of radiation, in other words a range of wavelengths, which neutral gases ($N_2$, $O_2$, $CO_2$) do not absorb is especially favourable since such constituents do not contribute to the calorific value of a gas in any way.

For example, the constituents $N_2$ and $O_2$ do not absorb in the infrared range and the constituent $CO_2$ does not absorb in one area of the infrared range.

It is therefore highly advantageous to use this physical quantity since it makes it possible to be concerned only with the constituents which contribute to the calorific value of a gas which is far simpler than having several different quantities to measure.

Depending on the composition of the gas and the required degree of accuracy for the calorific value, it may be sufficient to concerned only with the combustible constituent present in the highest proportion in the gas, for example methane or ethane or propane or butane or pentane.

To increase the accuracy of calorific value measurements, the apparatus used to determine the calorific value of the gas measures absorbance of electromagnetic radiation by other combustible constituents present in the gas.

Thus, for natural gas, in addition to measurement of the combustible constituent present in the largest quantity in the gas, for example methane, it is possible to measure, the absorbance of one or more other combustible constituents present in small quantities chosen from among ethane, propane, butane and pentane.

The various radiation wavelength(s) can be chosen such that the contribution made by a single combustible constituent of the gas or by several of these corresponds to each wavelength.

More particularly, the apparatus for determination of the calorific value of a gas comprises, over at least one area of flow of the gas:

at least one source of emission of electromagnetic radiation across said area of flow of gas, means for filtering said radiation, means for detecting said radiation attenuated by absorption due to the combustible constituent(s) of the gas for the corresponding wavelength(s), producing an electrical signal representative of this radiation for each wavelength in question, and electronic means for deducting the calorific value of the gas as well as the energy H(P,T) V(P,T) contained in the gas.

The means for filtering radiation can include one or more interferential filters, each of which being adapted to a different radiation wavelength for which at least one of said gas constituents shows absorption.

According to another possibility, the means for filtering radiation can include a filter that can be electrically tuneable on a wavelength range including at least one wavelength for which said gas constituent(s) shows absorption.

Electromagnetic radiation is, for example, situated in the infrared.

The range of wavelengths includes a wavelength(s) for which said gas constituent(s) shows absorption, for example between 1 and 12 $\mu$m.

When the principal constituent of the gas is methane, it is for example possible to concentrate on a wavelength range of 1.6 to 1.3 $\mu$m.

The invention also concerns a process for measurement of the calorific energy contained in a combustible gas transported in a pipe consisting in measuring a volume V of gas under pressure P and temperature T conditions of the gas circulating in said pipe and determining the calorific value H of the gas, characterised in that said process consists in measuring, under pressure P and temperature T conditions that are those under which the volume V(P,T) of gas is measured, at least one physical quantity proportional to the number of molecules of the various constituents of the gas in a given volume, and directly deducing the calorific value H(P,T) from this measurement under the same pressure P and temperature T conditions and then determining the calorific energy H(P,T) V(P,T) contained in the gas.

More particularly, the process according to the invention consists in measuring a physical quantity, which is the absorbance of electromagnetic radiation by at least one combustible constituent present in a large proportion in the gas for different wavelengths of said radiation.

The process according to the invention can also consist in measuring the absorbance of electromagnetic radiation by other combustible constituents present in the gas at different wavelengths of said radiation.

The process according to the invention consists in selecting the radiation wavelength(s) such that each wavelength corresponds to the contribution made by a single combustible constituent of the gas or by several of these.

More precisely, the process according to the invention consists in emitting electromagnetic radiation across at least one area of flow of gas, filtering said radiation, detecting the radiation attenuated by absorption due to the combustible constituent(s) of the gas for the corresponding wavelength(s), and producing an electrical signal representative of this radiation for each wavelength in question, and determining, from the signal or signals, the calorific value of the gas and the calorific energy H(P,T) V(P,T) contained in the gas.

The electromagnetic radiation is chosen such that the neutral gases ($N_2$, $O_2$, $CO_2$) do not absorb this radiation.

The radiation is, for example, chosen in the infrared range.

BRIEF DESCRIPTION OF THE DRAWINGS

Other characteristics and advantages of the invention appear from the following description of particular embodiments, given with reference to the accompanying drawings in which.

DETAILED DESCRIPTION OF THE PREFERRED EMBODIMENTS

Figure 1:
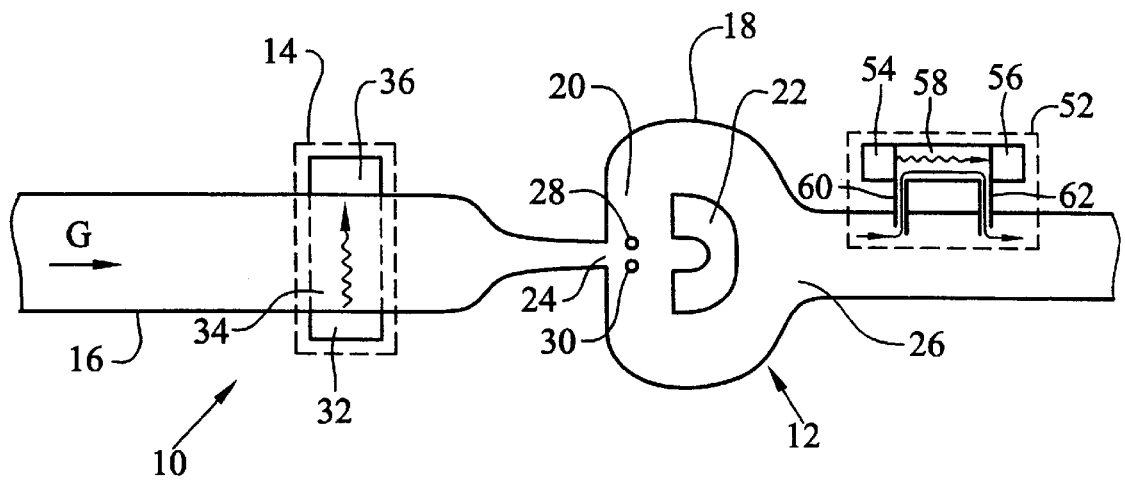
FIG. 1 is a general view of the energy-measuring device according to the invention.

As shown in FIG. 1 and designated by the general reference 10, a device for measuring the energy contained in a combustible gas, such as natural gas for example, comprises a gas meter 12 and an apparatus 14 for determination of the calorific value H of a gas.

Gas flow, shown by the arrow and designated by the letter G in FIG. 1, is transported in a pipe 16 where the device 10 is installed.

The gas meter 12 incorporates a measurement unit consisting of a fluid oscillator of a known type and described in detail in patent application number WO 97 35116.

This oscillator comprises an area 18 enclosing a chamber 20 in which an obstacle 22, as well as an inlet 24 and an outlet 26 are positioned, in order to allow the gas flow to enter or leave said chamber 20.

The inlet 24 is in the form of a narrow slit with respect to its length which is perpendicular to the plane of FIG. 2 in order to form a gas jet which oscillates in the chamber 20. Two calorific sensors 28, 30 (shown as circles in FIG. 1) detect the frequency of oscillation of the jet. This fluid oscillator functions according to the description given in WO 97 35116.

It should be noted that any type of gas meter can be used in place of this meter to achieve the aims of the present invention.

For example, a rotary displacement or deformable fanner volumetric gas meter or even a meter based on the principle of measuring the propagation time of an acoustic wave emitted in the flow between at least two acoustic transducers can be used here.

The gas meter measures a volume of gas V under the pressure P and temperature T conditions of the gas in pipe 16. The apparatus 14 is set up as close as possible to the gas meter, inside the measurement unit if possible, so that the calorific value H can be determined directly by this apparatus under the same pressure P and temperature T conditions as those under which measurement of gas volume takes place.

In this way, calorific energy or the combustion enthalpy of the gas is given by multiplying the two measurements V(P,T) and H(P,T) without the volume V being corrected in advance for pressure and temperature. The apparatus 14 can determine the calorific value H(P,T) directly under the pressure and temperature conditions which are those of the flow of gas in the line. This is possible since the apparatus measures at least one physical quantity which is proportional to the number of molecules of the various constituents of the gas in a given volume and this measurement can be carried out on molecules under pressure P and temperature T.

A method is known, for example from document EP 95308501.6, in which the determination of calorific energy requires measurement of four physical quantities density, speed of sound, calorific conductivity and viscosity.

Advantageously, the method for determining calorific value can be considerably simplified by choosing as the sole physical quantity the property of the combustible constituents of a gas of absorbing electromagnetic radiation for at least one wavelength of this radiation.

In such a case, contact with the gas is not necessary for measurement and the apparatus 14 for determination of calorific value can be installed directly in the pipe 16 without in any way disrupting the flow of gas.

Figure 2A:
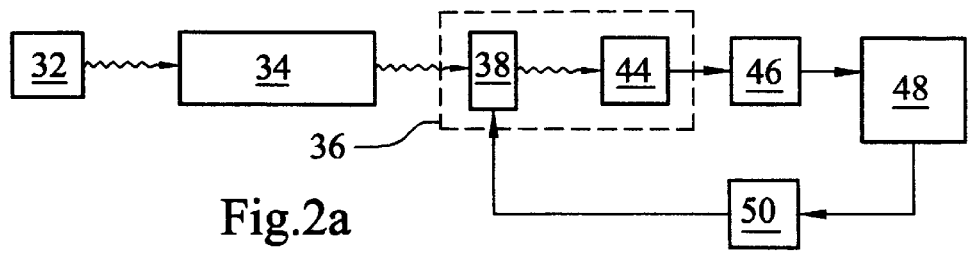
FIG. 2a represents a simplified diagram of the various elements constituting the apparatus.
Figure 2B:
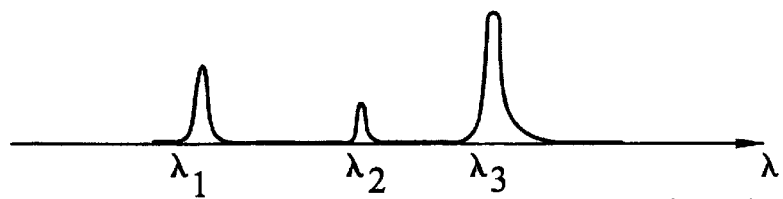
FIG. 2b is a diagrammatic representation of specific absorption rays for three different wavelengths.

As shown in FIGS 1 and 2a, this apparatus includes an electromagnetic radiation source 32 which emits radiation through a section 34 of the flow defined by the beam of said source.

The source 32 is mounted on one side of the pipe 16.

The apparatus 14 includes, on the opposite side of the pipe, a unit 36 which includes on the one hand means for filtering radiation attenuated by absorption by the combustible constituents of the gas and, on the other hand, means for detecting the attenuated and filtered radiation.

It should be noted that, as an alternative, the filtering means can be mounted on the same side as the source 32.

The filtering means can comprise one or more conventional interferential filters with each filter adapted to a particular wavelength.

A single filter can be used when the gas consists mainly, or even only, of methane and a few neutral gases. The filter is then adapted to filter radiation in the wavelength range characteristic of the absorption of methane.

Nevertheless, in most cases several filters are used either because absorption by other combustible constituents present in small quantities are to be measured in order to obtain a highly accurate estimation of the calorific value or because other combustible constituents present in the gas contribute significantly to the calorific value and not taking these into account would give a completely inaccurate calorific value.

Figure 2C:
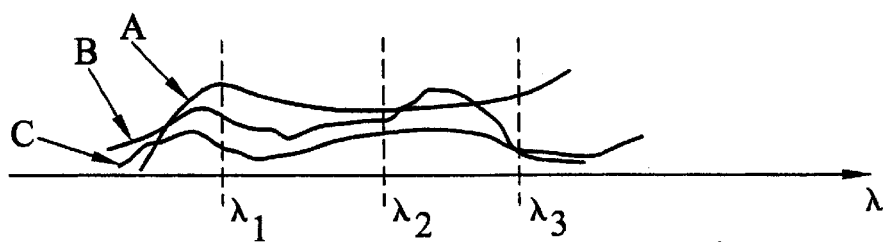
FIG. 2c is a diagrammatic representation of three absorption spectra A, B, C of various combustible constituents and their relative position with respect to three different wavelengths.

Each of the filters is adapted to a different radiation wavelength. The wavelengths, for example $\lambda_1, \lambda_2, \lambda_3$ can be chosen such that each wavelength corresponds to the spectrum of a single combustible constituent (FIG. 2b) or to the spectrum of several constituents (FIG. 2c). It is simpler to choose the first case as absorption by the corresponding constituent is directly obtained by the detection means.

In the second case, illustrated in FIG. 2c by the spectra (A, B, C) of three different combustible constituents, the absorbance measured is a function of the contribution of all constituents present at the wavelength in question ($\lambda_1, \lambda_2, \lambda_3$) and it is therefore necessary to resolve a system of equations where the unknowns are the number of moles of the various constituents per unit volume at pressure P and temperature T.

It is also important to ensure that wavelengths are chosen such that separate information concerning the contribution of each constituent is obtained for each wavelength.

Otherwise, the system of equations cannot be resolved.

These filters can, for example, be installed in a cylinder mounted on a rotating axis driven by a motor.

It is also possible to simplify the apparatus by using, in place of interferential filters, an electrically tuneable filter 38 over a range of wavelengths including the wavelength(s) for which the constituent(s) absorbs radiation.

The electromagnetic radiation chosen can be situated in the hyperfrequency range or in the optical range for example. In the optical range, this can be ultraviolet or infrared radiation.

More particularly, optical radiation is of the infrared type with particular attention paid to that part of the infrared spectrum in which the constituents $N_2$, $O_2$ and $CO_2$ do not show absorption.

The source 32 is for example a broad band-width source consisting of a tungsten filament.

The filter 38 can for example be tuned on a wavelength range of 3.2 to 3.6 $\mu$m.

Figure 3:
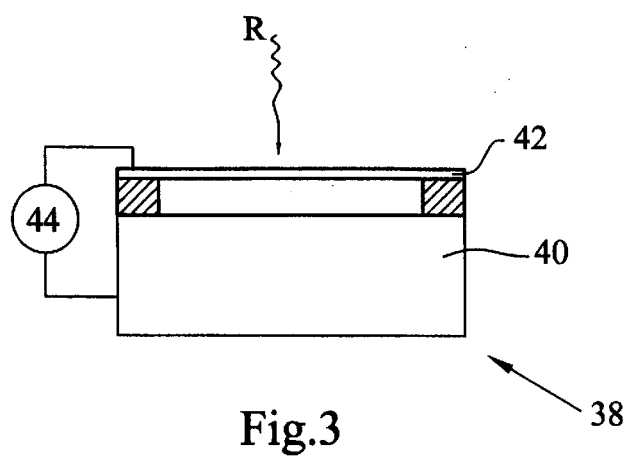
FIG. 3 is a diagrammatic representation of an electrically tuneable filter.

Such a filter is represented in FIG. 3 and is described in detail in European patent application 0 608 049. This filter, for example consisting of micro-machined silicon, comprises a fixed electrode 40 formed as a support and a mobile electrode 42, separated from each other by a given distance $e_0$ corresponding to the position in which the mobile electrode is not deformed.

In this position, called the resting position, the radiation shown by the arrow identified by the letter R in FIG. 3 is filtered for wavelength $\lambda_0$ equal to 2 $e_0$ (and for the harmonics of this wavelength).

A voltage source 44 is connected to the mobile and fixed electrodes and, when voltage is applied, the mobile electrode is deformed and comes closer to the fixed electrode. The distance between the electrodes is reduced to $e_1$ ($e_1 < e_0$) and the radiation is then filtered for the wavelength $\lambda_1$ equal to 2 $e_1$. In this way, the filter is tuned on various wavelengths for different electrical voltage values.

As shown in FIG. 2, the unit 36 also includes a broad band-width detector 44 such as a bolometer, thermocell or a photodiode.

The energy contained in the infrared radiation which crosses the gas and filter 38 is received by the detector 44 and transformed into an electrical signal representative of this radiation.

The signal is then amplified and converted into a numeric signal by the converter 46 then injected into the microprocessor 48.

An analogical numeric converter 50 is used to control the filter 38 and to choose the different wavelengths.

For the purpose of example, the gas is natural gas whose composition is given below with the corresponding calorific values given in kilo Joule per mole:

| | | |
|---|---|---|
| Methane | 89.5% | 891.09 |
| Ethane | 5% | 1561.13 |
| Propane | 1% | 2220.13 |
| Butane | 0.6% | 2873.97 |

-continued

| Pentane | 0.3% | 3527.8 |
| Neutral gases | 3.6% | |

The wavelengths are chosen as described earlier and are defined, for example, as follows:

$\lambda_1 = 3.2$ μm $\lambda_2 = 3.3$ μm $\lambda_3 = 3.4$ μm $\lambda_4 = 3.5$ μm $\lambda_5 = 3.6$ μm These wavelengths are such that the contribution of several combustible constituents corresponds to each of them.

By applying a voltage V of known value, for example equal to $2_0$ V, to the filter 38, the filter tunes on a wavelength $\lambda_1$ and the detector 44 gives an electrical signal corresponding to $S_1$ (V):

$$S_1(V) = \int E(\lambda) \theta gas(\lambda, x_i) \theta f(\lambda, V) Sd(\lambda) d\lambda$$

wherein $E(\lambda)$ designates light intensity emitted by the source 32, and $\theta gas(\lambda, x_i) = \exp(-L\Sigma\alpha_i(\lambda), x_i)$ designates the spectral response due to all gaseous combustible constituents present at this wavelength.

L designates the length of the optical path in the gas, $x_i$ represents the number of moles of combustible constituent i per unit volume at pressure P and temperature T, $\alpha_i$ designates the coefficient of absorption of the combustible constituent i and depends on wavelength, pressure and temperature, $\theta f(\lambda, V)$ represents optical transmission due to filter 38 and Sd represents the spectral response of the detector.

By tuning the filter 38 on different wavelengths $\lambda_1$ to $\lambda_5$ for different voltage values, values $S_1(V_1)$ to $S_5(V_5)$ are measured. Absorbance A is defined as follows A(V)=Ln(1/SV)) wherein Ln designates the Napierian logarithm, and the following five equation system is obtained:

$$A_1(V_1) = a_{11}x_1 + a_{21}x_2 + \ldots + a_{51}x_5$$

$$A_2(V_2) = a_{12}x_1 + a_{22}x_2 + \ldots + a_{52}x_5 \ldots$$

$$A_5(V_5) = a_{15}x_1 + a_{25}x_2 + \ldots + a_{55}x_5$$

where the terms $a_{ij}$ depend on the constituent i and the apparatus 14.

Before applying the invention to natural gas of unknown composition, a preliminary calibration step is carried out in the laboratory by injecting into apparatus 14 several gases with constituents whose number of moles per unit volume $x_i$ is known at given T and P values.

For each gas of known composition, the voltages $V_i$ (i=1, . . . ,5) are applied successively to the filter so that its spectral transmission tunes on wavelengths $\lambda_i$ (i=1, . . . ,5) and for each couple $V_i/\lambda_1$, is the detector provides a value $Si_1(V_i)$.

In this way, a five equation system is obtained for the first gas:

$$A_{11}(V_1) = a_{11}x_1 + \ldots + a_{51}x_5 \ldots$$

$$A_{51}(V_5) = a_{15}x_1 + \ldots + a_{55}x_5$$

where $x_i$(i=1, . . . ,5) are known and the terms $a_{ij}$ are not known.

By injecting foul other gases of known composition into the apparatus 14, twenty further equations are obtained with the same terms $a_{ij}$ as above.

This makes it possible to resolve by means of known mathematical methods, for example the linear equation resolution method, the following system of equations where the unknowns are the $a_{ij}$ coefficients:

$$[A_j] = [a_{ij}][x_i]$$

k=1, . . . ,5 k=1, . . . ,5 where the indices (k) identify the known gas mixture in question.

By reversing the matrix $[a_{ij}]$ using a conventional mathematical inversion method, the following system is obtained:

$$[x_i] = [a_{ij}]^{-1}[A_j] = [b_{ij}][A_j]$$

x=1, . . . ,5 i=1, . . . ,5 i=1, . . . ,5 j=1, . . . ,5 i=1, . . . ,5 i=1, . . . ,5 j=1, . . . ,5

In this way, the values x, are given by $x_i = \Sigma b_{ij} A_j(V)$, j=1, . . . ,5

All that needs to be done is to enter the data $b_{ij}$ calculated during calibration into the memory of the microprocessor 48 and when natural gas of unknown composition, and therefore of unknown calorific value, is transported in pipe 16, the different values Aj(V) are measured for different filter wavelengths obtained for the corresponding voltage values and the terms $x_i$ can be easily deduced. The calorific value H(P,T) of the gas is given by $\Sigma x_i H_i$ where $H_i$ represents the calorific value of constituent i in Joules per mole.

i=1, . . . ,5

Consequently, once the terms xi are determined, the calorific value H(P,T) is obtained directly.

The energy H(P,T) V(P,T) is then deduced from the preceding information.

The apparatus used to determine calorific energy can also be positioned, for example, downstream to the fluid oscillator chamber 20 and designated by the general reference 52 (FIG. 1).

This apparatus, in the same way as apparatus 14, comprises a source 54, filtering means and detection means 56 as well as a chamber 58 filled with gas and placed between the source 54 and the means 56.

The apparatus 52 is mounted on the pipe 16 by means of two connectors 60, 62 which allow respectively some of the gas flow to be brought into the chamber 58 and to return it to said pipe. The connector 60 has an area which opens into the pipe at a distance from the wall of the pipe in order to carry out sampling of the gas whose composition is representative of the gas flow.

Installation of apparatus 58 is advantageous since having two cut-off valves on each of the connectors 60, 62 makes it easy to remove said apparatus, for example for maintenance, without stopping gas circulation in the pipe and therefore by continuing to measure gas volume V(P,T).

Figure 4:
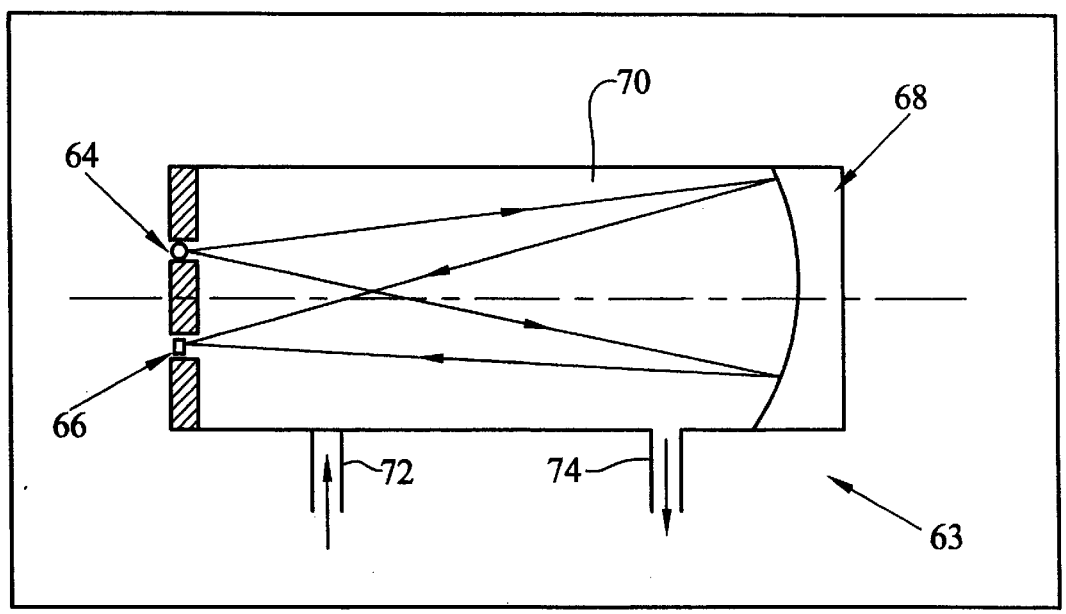
FIG. 4 is a view of a variant of the apparatus.

FIG. 4 illustrates a variant of apparatus 63 for determination of calorific value in which the source 64, filtering and detection means 66 are on the same side of said apparatus.

A mirror 68, lot example spherical, is placed at the opposite side of the apparatus in order to reflect radiation emitted by the source onto the means 66. A chamber 70 filled with gas is placed between the mirror 68 on one hand and the source 64 and means 66 on the other.

Two connectors 72, 74 are provided for in order to introduce and evacuate the gas in the chamber 70.

This apparatus can also be mounted directly in the same way as apparatus 52 in FIG. 1.

However, it is possible to envisage positioning this apparatus in the same way as apparatus 14 by eliminating the chamber 70 and the connectors 72, 74 because the flow of gas in the pipe would then circulate between the mirror 68, and the source 64 and means 66.

The apparatus can also be installed at another point in the fluid oscillator and, for example, upright to inlet 24 forming a slit.

What is claimed is:

1. Device for measuring calorific energy contained in a combustible gas transported in a pipe, the device comprising:
   a gas meter for measuring a volume V of gas under a pressure P and a temperature T while gas is circulating in said pipe;
   means for measuring at least one physical quantity proportional to the number of molecules of at least one of various constituents of the gas in a given volume, said means for measuring being located in close proximity to said gas meter; and
   means for determining, as a function of said at least one measured physical quantity, the calorific energy H(P,T) V(P,T) of the gas when the gas is under the same pressure P and temperature T conditions as those in which the volume V(P,T) of the gas is measured.

2. Device according to claim 1, wherein the at least one physical quantity that is measured is the absorbance of electromagnetic radiation by a combustible constituent present in a large proportion of the gas for at least one wavelength of said electromagnetic radiation; and
   wherein said determining means deduces the calorific energy from this absorption measurement.

3. Device according to claim 2, wherein the means for measuring the at least one physical quantity also measures the absorbance of electromagnetic radiation by other combustible constituents present in the gas for different wavelengths of said electromagnetic radiation.

4. Device according to claim 3, wherein the different wavelengths of said electromagnetic radiation are chosen such that each of said different wavelengths corresponds to the contribution made by a single combustible constituent.

5. Device according to claim 3, wherein each of the different wavelengths of said electromagnetic radiation corresponds to the contribution made by several combustible constituents.

6. Device according to claim 2,
   wherein the means for measuring the at least one physical quantity is positioned, over at least one area of flow of the gas and includes:
   at least one electromagnetic radiation source for emitting electromagnetic radiation across said area of flow of gas,
   means for filtering said radiation,
   means for detecting said radiation attenuated by absorption due to the at least one combustible constituent of the gas for the corresponding at least one wavelength, and for producing an electrical signal representative of this radiation for the wavelength in question, and
   wherein said means for determining the calorific energy of the gas includes:
   electronic circuitry for determining a calorific value of the gas as well as the energy H(P,T) V(PIT) contained in the gas.

7. Device according to claim 6, wherein the means for filtering said radiation includes at least one interferential filter which is adapted to a radiation wavelength for which at least one of said gas constituents shows absorption.

8. Device according to claim 6, wherein the means for filtering said radiation comprise a filter electrically tuneable on a wavelength range including at least one wavelength for which said at least one gas constituent shows absorption.

9. Device according to claim 2, wherein the electromagnetic radiation is situated in the infrared range.

10. Device according to claims 8 and 9, wherein the range of the wavelengths include at least one wavelength for which said at least one gas constituent shows absorption between 1 and 12 $\mu$m.

11. Device according to claim 2, wherein the electromagnetic radiation is chosen such that the neutral gases, $N_2$, $O_2$, and $CO_2$ do not absorb this radiation.

12. Device according to claim 1,
    wherein a constituent of said gas is methane, and
    wherein the calorific value of methane is used by said means for determining the calorific energy of the gas.

13. Device according to claim 1,
    wherein a constituent of said gas is ethane, and
    wherein the calorific value of ethane is used by said means for determining the calorific energy of the gas.

14. Device according to claim 1,
    wherein a constituent of said gas is propane, and
    wherein the calorific value of propane is used by said means for determining the calorific energy of the gas.

15. Device according to claim 1,
    wherein a constituent of said gas is butane, and
    wherein the calorific value of butane is used by said means for determining the calorific energy of the gas.

16. Device according to claim 1,
    wherein a constituent of said gas is pentane, and
    wherein the calorific value of pentane is used by said means for determining the calorific energy of the gas.

17. Device according to claim 1, wherein the combustible gas is natural gas.

18. Device according to claim 1, wherein the means for measuring at least one physical quantity, and means for determining the calorific energy H(P,T) of a gas are integrated into the gas meter.

19. A method for measuring the calorific energy contained in a combustible gas transported in a pipe, the method comprising:
    measuring a volume V of gas under pressure P and temperature T while the gas is circulating in said pipe;
    measuring, under the same pressure P and temperature T conditions under which the volume V(P,T) of the gas is measured, at least one physical quantity proportional to the number of molecules of the various constituents of the gas in a given volume;
    directly deducing the calorific value H(P,T) from said measurement; and
    determining the energy H(P,T) V(P,T) contained in the gas using the deduced calorific value H(P,T).

20. Method according to claim 19, wherein the step of measuring the at least one physical quantity includes:
    measuring the absorbance of electromagnetic radiation by at least one combustible constituent present in a large proportion in the gas for at least one wavelength of said electromagnetic radiation.

21. Method according to claim 20, wherein the step of measuring the at least one physical quantity includes:
    measuring the absorbance of electromagnetic radiation by other combustible constituents present in the gas for different wavelengths of said electromagnetic radiation.

22. Method according to claim 21, further comprising:
selecting the different wavelengths of said electromagnetic radiation such that each wavelength corresponds to the contribution made by a single combustible constituent.

23. Method according to claim 21, further comprising:
selecting the different wavelengths of said electromagnetic radiation such that each wavelength corresponds to the contribution made by several combustible constituents.

24. Method according to claim 20,
wherein the step of measuring at least one physical quantity includes:
emitting electromagnetic radiation across at least one area of flow of gas,
filtering said electromagnetic radiation,
detecting said electromagnetic radiation attenuated by absorption due to the at least one combustible constituent of the gas for the corresponding at least one wavelength and producing an electrical signal representative of this radiation for the wavelength in question, and
wherein the step of directly deducing the calorific value H(P,T) includes:
determining from the produced electrical signal the calorific value H(P,T).

25. Method according to claim 20, wherein the electromagnetic radiation is chosen such that the neutral gases, $N_2$, $O_2$, and $CO_2$, do not absorb said electromagnetic radiation.

26. Method according to claim 20, wherein the electromagnetic radiation is situated in the infrared range.

* * * * *